United States Patent
Yap et al.

(10) Patent No.: US 12,030,860 B2
(45) Date of Patent: Jul. 9, 2024

(54) METHOD FOR PRODUCING EPOXYALKANE, AND SOLID OXIDATION CATALYST

(71) Applicant: KAO CORPORATION, Tokyo (JP)

(72) Inventors: Mee Lin Yap, Wakayama (JP); Shingo Takada, Wakayama (JP)

(73) Assignee: KAO CORPORATION, Tokyo (JP)

( * ) Notice: Subject to any disclaimer, the term of this patent is extended or adjusted under 35 U.S.C. 154(b) by 834 days.

(21) Appl. No.: 17/264,466

(22) PCT Filed: Jun. 11, 2019

(86) PCT No.: PCT/JP2019/023111
§ 371 (c)(1),
(2) Date: Jan. 29, 2021

(87) PCT Pub. No.: WO2020/026599
PCT Pub. Date: Feb. 6, 2020

(65) Prior Publication Data
US 2021/0317098 A1 Oct. 14, 2021

(30) Foreign Application Priority Data
Jul. 30, 2018 (JP) .................................. 2018-142795

(51) Int. Cl.
*C07D 301/12* (2006.01)
*B01J 31/34* (2006.01)
*B01J 37/00* (2006.01)
*B01J 37/04* (2006.01)
*B01J 37/08* (2006.01)
*B01J 37/30* (2006.01)

(52) U.S. Cl.
CPC .......... *C07D 301/12* (2013.01); *B01J 31/34* (2013.01); *B01J 37/0027* (2013.01); *B01J 37/009* (2013.01); *B01J 37/04* (2013.01); *B01J 37/086* (2013.01); *B01J 37/30* (2013.01); *B01J 2231/72* (2013.01)

(58) Field of Classification Search
CPC ..... C07D 301/12; B01J 31/34; B01J 37/0027; B01J 37/009; B01J 37/04; B01J 37/086; B01J 37/30; B01J 2231/72
See application file for complete search history.

(56) References Cited

U.S. PATENT DOCUMENTS

| 3,829,392 A | 8/1974 | Wulff |
| 4,657,884 A * | 4/1987 | Luft .................. C07C 51/56 502/154 |
| 2008/0146826 A1 | 6/2008 | Kaminsky et al. |
| 2012/0108830 A1 | 5/2012 | Takumi et al. |

FOREIGN PATENT DOCUMENTS

| DE | 34 40 646 A1 | 5/1986 |
| GB | 1 339 309 A | 12/1973 |
| JP | 47-7315 A | 4/1972 |
| JP | 61-114741 A | 6/1986 |
| JP | 2001-17864 A | 1/2001 |

OTHER PUBLICATIONS

Xie, Chem Biochem Eng Q, vol. 22(1), 2008, 25-39. (Year: 2008).*
Somma, 2004, J of Catalysis, VOI 227, 344-351. (Year: 2004).*
International Search Report (PCT/ISA/210) issued in PCT/JP2019/023111, dated Sep. 10, 2019.
English translation of the Chinese Search Report for Chinese Application No. 201980050407.6, dated Apr. 29, 2023.
International Preliminary Report on Patentability and English translation of the Written Opinion of the International Searching Authority, dated Feb. 11, 2021, for International Application No. PCT/JP2019/023111.
Extended European Search Report for European Application No. 19845509.9, dated Mar. 30, 2022.
Somma et al., "Oxidation of geraniol and other substituted olefins with hydrogen peroxide using mesoporous, sol-gel-made tungsten oxide-silica mixed oxide catalysts," Journal of Catalysts, vol. 227, 2004, pp. 344-351.

(Continued)

*Primary Examiner* — D Margaret M Seaman
(74) *Attorney, Agent, or Firm* — Birch, Stewart, Kolasch & Birch, LLP

(57) ABSTRACT

The present invention provides: a method for producing an epoxyalkane capable of obtaining an epoxide in a high yield while attaining a high olefin conversion rate and a high selectivity for epoxides even when an olefin includes a long carbon chain, and a solid oxidation catalyst used in the method. The method for producing an epoxyalkane of the present invention comprises reacting an olefin with an oxidant in the presence of a solid oxidation catalyst, wherein the solid oxidation catalyst comprises a transition metal and a carrier that supports the transition metal, and the carrier is a metal oxide having a silyl group represented by the following general formula (1):

$$R^1R^2R^3Si—  \quad (1)$$

wherein $R^1$, $R^2$, and $R^3$ are each independently a single bond, a hydrocarbon group, a halogenated hydrocarbon group, an alkoxy group, or a halogen, and at least one of $R^1$, $R^2$, and $R^3$ is a hydrocarbon group having 3 or more carbon atoms or a halogenated hydrocarbon group having 3 or more carbon atoms.

20 Claims, No Drawings

(56) References Cited

OTHER PUBLICATIONS

Xie et al., "A Review on Heterogeneous Solid Catalysts and Related Catalytic Mechanisms for Epoxidation of Olefins with H2O2," Chem. Biochem. Eng. Q., vol. 22, No. 1, 2008, pp. 25-39.

Xie et al., "Transesterification of soybean oil over WO3 supported on AlPO4 as a solid acid catalyst," Bioresource Technology, vol. 119, May 22, 2012 (published online May 30, 2012), pp. 60-65.

Yan et al., "Gold supported on microporous aluminophosphate AlPO4-H1 for selective oxidation of CO in a H2-rich stream," Studies in Surface Science and Catalysis, vol. 170, 2007, pp. 1065-1071.

* cited by examiner

METHOD FOR PRODUCING EPOXYALKANE, AND SOLID OXIDATION CATALYST

TECHNICAL FIELD

The present invention relates to a method for producing an epoxyalkane by reacting an olefin with hydrogen peroxide in the presence of a solid oxidation catalyst, and to the solid oxidation catalyst used in the method.

BACKGROUND ART

A method of epoxidizing an olefin using hydrogen peroxide is known. This method generally has problems that both the olefin conversion rate and the selectivity for epoxides are low.

For aiming at selectively producing only epoxides, JP-A-2001-17864 discloses a method for producing an epoxidized product using an epoxidation catalyst that is a salt obtained by the reaction between: (1) a surface-treated carrier obtained by reacting (a) an activated carbon or an inorganic solid having a functional group capable of being reacted with a silane coupling agent, with (b) a silane coupling agent having an alkyl group substituted with a functional group capable of being reacted with a tertiary amine to form a quaternary ammonium salt, and reacting the reaction product with a tertiary amine or a cyclic amine; and (2) a heteropolyacid having a group V atom in the periodic table and a tungsten atom in its molecule.

SUMMARY OF THE INVENTION

However, in the method for producing an epoxidized product of JP-A-2001-17864, it is found that when an olefin includes a short carbon chain, the olefin had a high conversion rate and a high selectivity for epoxides, but when the olefin includes a long carbon chain, the catalytic activity of the epoxidation catalyst was greatly reduced and the epoxidation reaction hardly proceeded or the olefin conversion rate was greatly reduced.

The present invention has been made in view of the above circumstances, and provides a method for producing an epoxyalkane capable of obtaining an epoxide in a high yield while attaining a high olefin conversion rate and a high selectivity for epoxides even when an olefin includes a long carbon chain, and a solid oxidation catalyst used in the method.

As a result of intensive studies, the present inventor has found that the above problems can be solved by the following method for producing an epoxyalkane, and the following solid oxidation catalyst.

That is, the present invention is related to a method for producing an epoxyalkane, which method comprises reacting an olefin with an oxidant in the presence of a solid oxidation catalyst, wherein
the solid oxidation catalyst comprises a transition metal and a carrier that supports the transition metal, and
the carrier is a metal oxide having a silyl group represented by the following general formula (1):

$$R^1R^2R^3Si- \qquad (1)$$

wherein $R^1$, $R^2$, and $R^3$ are each independently a single bond, a hydrocarbon group, a halogenated hydrocarbon group, an alkoxy group, or a halogen, and at least one of $R^1$, $R^2$, and $R^3$ is a hydrocarbon group having 3 or more carbon atoms or a halogenated hydrocarbon group having 3 or more carbon atoms.

Also, the present invention is related to a solid oxidation catalyst that is used in a method for producing an epoxyalkane by reacting an olefin with an oxidant, wherein
the solid oxidation catalyst comprises a transition metal and a carrier that supports the transition metal, and
the carrier is a metal oxide having a silyl group represented by the following general formula (1):

$$R^1R^2R^3Si- \qquad (1)$$

wherein $R^1$, $R^2$, and $R^3$ are each independently a single bond, a hydrocarbon group, a halogenated hydrocarbon group, an alkoxy group, or a halogen, and at least one of $R^1$, $R^2$, and $R^3$ is a hydrocarbon group having 3 or more carbon atoms or a halogenated hydrocarbon group having 3 or more carbon atoms.

According to the method for producing an epoxyalkane of the present invention, a desired epoxide can be obtained in a high yield while attaining a high olefin conversion rate and a high selectivity for epoxides even when a raw material olefin has a long carbon chain.

MODE FOR CARRYING OUT THE INVENTION

Hereinafter, the present invention will be described in detail.

Solid Oxidation Catalyst

The solid oxidation catalyst of the present invention comprises a transition metal and a carrier that supports the transition metal, and
the carrier is a metal oxide having a silyl group represented by the following general formula (1):

$$R^1R^2R^3Si- \qquad (1)$$

wherein $R^1$, $R^2$, and $R^3$ are each independently a single bond, a hydrocarbon group, a halogenated hydrocarbon group, an alkoxy group, or a halogen, and at least one of $R^1$, $R^2$, and $R^3$ is a hydrocarbon group having 3 or more carbon atoms or a halogenated hydrocarbon group having 3 or more carbon atoms.

The transition metal is supported on the carrier in the form of a simple substance, a compound, or an ion.

The transition metal is a metal element of groups 3 to 12 of the periodic table, and specific examples of the transition metal include a group 3 element (Sc, Y, etc.), a group 4 element (Ti, Zr, Hf), a group 5 element (V, Nb, Ta), a group 6 element (Cr, Mo, W), a group 7 element (Mn, Tc, Re), a group 8 element (Fe, Ru, Os), a group 9 element (Co, Rh, Ir), a group 10 element (Ni, Pd, Pt), a group 11 element (Cu, Ag, Au), and a group 12 element (Zn, Cd, Hg). These metals may be used alone or in combination of two or more thereof. Of these, a metal element of groups 4 to 8 is preferred, a group 6 metal element is more preferred, and W is still more preferred.

The compound of the transition metal is not particularly limited, and examples thereof include hydroxides, oxides, halides (e.g., fluorides, chlorides, bromides, iodides, etc.), oxo acid salts (e.g., nitrates, sulfates, phosphates, borates, carbonates, etc.), isopoly acid salts, heteropoly acid salts, and organic acid salts (e.g., acetates, propionates, cyanides, naphthenates, stearates, alkylsulfonates, arylsulfonates, etc.) of the transition metals.

The transition metal compound is preferably a tungsten compound from the viewpoint of catalytic activity.

Examples of the tungsten compound include tungstic acids or salts thereof (e.g. tungstic acid, sodium tungstate, potassium tungstate, lithium tungstate, ammonium tungstate, etc.); dodecatungstates (e.g. sodium dodecatungstate, potassium dodecatungstate, ammonium dodecatungstate, etc.); and heteropolyacids or salts thereof containing tungsten atoms (e.g. phosphotungstic acid, sodium phosphotungstate, silicotungstic acid, sodium silicotungstate, phosphovanadotungstate, phosphomolybdotungstate, etc.). These may be used alone or in combination of two or more thereof. Of these, tungstic acid or a salt thereof is preferable.

The carrier is a metal oxide having a silyl group represented by the following general formula (1):

$R^1R^2R^3Si-$ (1)

wherein $R^1$, $R^2$, and $R^3$ are each independently a single bond, a hydrocarbon group, a halogenated hydrocarbon group, an alkoxy group, or a halogen, and at least one of $R^1$, $R^2$, and $R^3$ is a hydrocarbon group having 3 or more carbon atoms or a halogenated hydrocarbon group having 3 or more carbon atoms. The hydrophobicity of the carrier can be adjusted by the type of organic groups (for example, hydrocarbon group, halogenated hydrocarbon group, and alkoxy group) contained in the silyl group. As a result, the olefin conversion rate can be increased even when the olefin has a long carbon chain.

The metal oxide is not particularly limited, but from the viewpoint of catalytic activity, an oxide containing a metal element having a period of 3 to 5 cycles in the periodic table is preferable, an oxide containing one or more metal elements selected from Mg, Al, Si, Ti, Fe, Zn, Ga, Y, Zr, and Sn is more preferable, and an oxide containing Al is still more preferable. These may be used alone or in combination of two or more thereof.

Specific examples of the metal oxide include silica, alumina, titania, magnesia, zirconia, aluminum phosphate, silicoaluminophosphate, and metallic aluminum phosphate (the metals include, for example, titanium, iron, magnesium, zinc, manganese, cobalt, etc.). These metal oxides may be used alone or in combination of two or more thereof.

Examples of the silica include glassy silica, quartz, diatomaceous earth, amorphous silica, silica gel, silica powder, silica sol, various coated silica fine particles (zeolite, etc.) whose silica surface is coated with aluminum or the like, silica-coated fine particles in which the surface of resin particles or metal oxide sol is coated with silica, spherical silica fine particles, rod-shaped silica fine particles, and necklace-shaped silica fine particles in which spherical silica is connected.

Examples of the alumina include α-alumina, gibbsite, bayerite, boehmite, β-alumina, γ-alumina, and amorphous alumina.

Examples of the titania include rutile-type titania and anatase-type titania.

Examples of the magnesia include magnesium carbonate (magnesite), molten magnesia obtained by melting or calcining magnesium carbonate extracted from seawater, sintered magnesia, light-baked magnesia, and calcined magnesia.

Examples of the zirconia include partially stabilized zirconia containing $ZrO_2$ as a main component and one or more stabilizers such as CaO, MgO, or $Y_2O_3$.

The metal oxide may be a composite with phosphonic acid. Here, the composite means a metal oxide in which a part of the skeletal structure is replaced with phosphonic acid.

The metal oxide preferably contains phosphoric acid from the viewpoint of forming a composite with phosphonic acid, and more preferably contains Al and/or phosphoric acid from the viewpoint of catalytic activity and of forming a composite with phosphonic acid, and is still more preferably aluminum phosphate from the viewpoint of catalytic activity and of forming a composite with a phosphonic acid.

The phosphonic acid used is not particularly limited, but is preferably an organic phosphonic acid having a saturated or unsaturated hydrocarbon group having 1 or more and 18 or less carbon atoms, more preferably one or more selected from an alkylphosphonic acid having an alkyl group of 2 to 18 carbon atoms and an aryl phosphonic acid, and still more preferably an alkylphosphonic acid having an alkyl group of 2 to 18 carbon atoms, from the viewpoint of catalytic activity. The alkyl group having 1 or more and 18 or less carbon atoms is not particularly limited, and examples thereof include a methyl group, an ethyl group, a propyl group, a butyl group, a pentyl group, a hexyl group, a heptyl group, a 2-ethylhexyl group, an octyl group, a nonyl group, a decyl group, an undecyl group, a dodecyl group, a tridecyl group, a tetradecyl group, a pentadecyl group, a hexadecyl group, a heptadecyl group, and an octadecyl group. Examples of the aryl group include a phenyl group, a benzyl group, a tolyl group, a xylyl group, a naphthyl group, and a biphenyl group. When the phosphonic acid is an organic phosphonic acid, the hydrophobicity of the carrier can be adjusted by the type of the organic group (for example, hydrocarbon group, halogenated hydrocarbon group, and alkoxy group) of the organic phosphonic acid. As a result, the olefin conversion rate can be increased even when the carbon chain of the olefin is long.

Examples of the method for preparing the composite of the metal oxide and the phosphonic acid include a precipitation method and a method of impregnating a metal oxide with phosphonic acid, and the precipitation method is preferred.

Hereinafter, as a specific example of the method for preparing the composite, a method for preparing a composite of aluminum phosphate and an organic phosphonic acid ($RPOO_2AlPO_4$) by a precipitation method will be described.

In the precipitation method, first, an aqueous solution (S) containing a water-soluble aluminum salt (for example, $Al(NO_3)_3 \cdot 9H_2O$, etc.), phosphoric acid, and an organic phosphonic acid is mixed with an alkali (T). When the solubility of the organic phosphonic acid is poor, the aqueous solution (S) may be prepared by appropriately adding a solvent such as alcohol or acetone.

The molar ratio (Al/P) of Al in the water-soluble aluminum salt to P in the phosphoric acid and organic phosphonic acid is preferably 0.6 or more, more preferably 0.7 or more, still more preferably 0.8 or more, even still more preferably 0.9 or more, and is preferably 10 or less, more preferably 5 or less, still more preferably 2 or less, even still more preferably less than 1, from the viewpoint of reactivity.

From the viewpoint of reactivity, the molar ratio of the organic phosphonic acid to the phosphoric acid (organic phosphonic acid/phosphoric acid) is preferably 0.05 or more, more preferably 0.1 or more, still more preferably 0.2 or more, even still more preferably 0.3 or more, and is preferably 5 or less, more preferably 3 or less, still more preferably 1 or less, even still more preferably 0.5 or less.

The alkali (T) is not particularly limited, and examples thereof include inorganic bases such as sodium hydroxide, potassium hydroxide, sodium carbonate, potassium carbonate, sodium hydrogen carbonate, and potassium hydrogen carbonate, ammonia, and urea. From the viewpoint of reactivity, ammonia is preferable. These alkalis (T) are usually used as an aqueous solution.

The method of mixing the aqueous solution (S) and the alkali (T) is not particularly limited, but from the viewpoint of reactivity, a method of dropping the alkali (T) into the aqueous solution (S) is preferable. From the viewpoint of reactivity and productivity, the dropping time is preferably 0.5 hours or more, more preferably 1 hour or more, still more preferably 2 hours or more, even still more preferably 3 hours or more, and is preferably 15 hours or less, more preferably 10 hours or less, still more preferably 5 hours or less. The reaction temperature is preferably 20° C. or higher, more preferably 25° C. or higher, and is preferably 80° C. or lower, more preferably 60° C. or lower, still more preferably 40° C. or lower, from the viewpoint of reactivity and productivity.

By mixing the aqueous solution (S) and the alkali (T) and adjusting the pH, a precipitate of a composite $(RPOO_2AlPO_4)$ of aluminum phosphate with an organic phosphonic acid can be obtained. From the viewpoint of reactivity, the pH in the pH adjustment is preferably 4.0 or more, more preferably 4.5 or more, still more preferably 5.0 or more, and is preferably 10.0 or less, more preferably 8.0 or less, still more preferably 6.0 or less.

The precipitate is preferably aged in the reaction solution. The aging time is preferably 0.5 hours or more, more preferably 1 hour or more, and is preferably 10 hours or less, more preferably 5 hours or less, still more preferably 3 hours or less, from the viewpoint of reactivity and productivity.

After that, the precipitate is filtered, washed with water as needed, and dried.

The dried precipitate may be calcined. From the viewpoint of reactivity, the calcination temperature is preferably 250° C. or higher, more preferably 300° C. or higher, still more preferably 350° C. or higher, and is preferably 500° C. or lower, more preferably 450° C. or lower, still more preferably 400° C. or lower. From the viewpoint of reactivity and productivity, the calcination time is preferably 1 hour or more, more preferably 2 hours or more, still more preferably 3 hours or more, and is preferably 10 hours or less, more preferably 7 hours or less, still more preferably 5 hours or less. The atmosphere at the time of calcination is not particularly limited, but from the viewpoint of reactivity, the calcination is preferably carried out in the presence of air or oxygen.

The shape of the carrier is not particularly limited, and examples thereof include powders, granules, noodles, and pellets.

When the carrier is in the form of a powder, the average particle size is preferably 1 μm or more, more preferably 3 μm or more, still more preferably 5 μm or more, even still more preferably 7 μm or more, and is preferably 300 μm or less, more preferably 200 μm or less, still more preferably 100 μm or less, even still more preferably 30 μm or less, from the viewpoint of catalytic activity.

When the carrier is in the form of granules, the average particle size is preferably 0.2 mm or more, more preferably 0.4 mm or more, still more preferably 0.6 mm or more, and is preferably 2.0 mm or less, more preferably 1.3 mm or less, still more preferably 0.8 mm or less, from the viewpoint of catalytic activity and ease of recovery.

When the carrier is in the form of a noodle, the diameter is preferably 1.0 mm or more, more preferably 1.2 mm or more, still more preferably 1.4 mm or more, and is preferably 2.5 mm or less, more preferably 2.0 mm or less, still more preferably 1.5 mm or less, from the viewpoint of catalyst strength and catalytic activity.

When the carrier is in the form of a noodle, the length is preferably 2 mm or more, more preferably 3 mm or more, and is preferably 8 mm or less, more preferably 6 mm or less, still more preferably 4 mm or less, from the viewpoint of uniformity at the time of filling and catalyst strength.

When the carrier is in the form of a pellet, the length is preferably 1.5 mm or more, more preferably 2.0 mm or more, still more preferably 2.5 mm or more, and is preferably 5.0 mm or less, more preferably 4.0 mm or less, still more preferably 3.0 mm or less, from the viewpoint of catalyst strength and catalytic activity.

The specific surface area of the carrier is preferably 30 $m^2/g$ or more, more preferably 50 $m^2/g$ or more, still more preferably 80 $m^2/g$ or more, and is preferably 250 $m^2/g$ or less, more preferably 190 $m^2/g$ or less, still more preferably 140 $m^2/g$ or less, from the viewpoint of catalytic activity and selectively obtaining epoxides.

The average pore diameter of the carrier is preferably 2 nm or more, more preferably 3 nm or more, still more preferably 4 nm or more, and is preferably 15 nm or less, more preferably 10 nm or less, still more preferably 7 nm or less, from the viewpoint of catalytic activity and selectively obtaining epoxides.

The solid oxidation catalyst of the present invention can be prepared, for example, by supporting the transition metal on the metal oxide and then silylating the metal oxide with a silylating agent.

The method for supporting the transition metal on the metal oxide is not particularly limited, and known methods can be adopted and examples thereof include a precipitation method, an impregnation method, a spraying method, an adsorption method, and a pore filling method, among which an impregnation method is preferred.

Hereinafter, as a specific example, a method for supporting tungstic acid on the metal oxide by an impregnation method will be described.

In the impregnation method, first, tungstic acid and an alkali are mixed to prepare an aqueous tungstic acid solution. The alkali is not particularly limited, and examples thereof include inorganic bases (e.g. sodium hydroxide, potassium hydroxide, sodium carbonate, potassium carbonate, sodium hydrogen carbonate, and potassium hydrogen carbonate), ammonia, and urea. From the viewpoint of reactivity, ammonia is preferred. These alkalis are usually used as an aqueous solution. Then, the prepared aqueous tungstate solution and the metal oxide are mixed to support the tungstic acid on the metal oxide. If the metal oxide is difficult to disperse in the aqueous tungstate solution, a solvent such as alcohol or acetone may be added as appropriate.

After that, water and solvent in the aqueous solution are distilled off. The metal oxide supporting tungstic acid (hereinafter, referred to as W-supported metal oxide) is washed with water if necessary and dried. The W-supported metal oxide after drying may be pulverized.

Alternatively, the W-supported metal oxide after drying may be calcined. The calcination temperature is preferably 150° C. or higher, more preferably 200° C. or higher, still more preferably 300° C. or higher, and is preferably 500° C. or lower, more preferably 450° C. or lower, still more preferably 400° C. or lower, from the viewpoint of catalytic activity and selectively obtaining epoxides. The calcination time is preferably 1 hour or more, more preferably 2 hours or more, still more preferably 3 hours or more, and is preferably 10 hours or less, more preferably 7 hours or less, still more preferably 5 hours or less, from the viewpoint of catalytic activity and selectively obtaining epoxides. The atmosphere at the time of calcination is not particularly limited, but the calcination is preferably carried out in the presence of air or oxygen from the viewpoint of catalytic activity and selectively obtaining epoxides.

Examples of the silylating agent include a silylating agent represented by the following general formula (2):

$$R^1R^2R^3SiX \qquad (2)$$

wherein $R^1$, $R^2$, and $R^3$ are each independently a hydrocarbon group, a halogenated hydrocarbon group, an alkoxy group, or a halogen; at least one of $R^1$, $R^2$, and $R^3$ is a hydrocarbon group having 3 or more carbon atoms or a halogenated hydrocarbon group having 3 or more carbon atoms; and X is an alkoxy group or a halogen.

The hydrocarbon group is not particularly limited, and examples thereof include a saturated or unsaturated aliphatic hydrocarbon group, a saturated or unsaturated alicyclic hydrocarbon group, and an aromatic hydrocarbon group. The number of carbon atoms of each of the aliphatic hydrocarbon group and the alicyclic hydrocarbon group is not particularly limited, but from the viewpoint of catalytic activity and selectively obtaining an epoxide, the number of carbon atoms of said groups is preferably 3 or more, more preferably 6 or more, still more preferably 8 or more, and is preferably 22 or less, more preferably 18 or less, still more preferably 12 or less. Examples of the aromatic hydrocarbon group include a phenyl group, a benzyl group, a tolyl group, a xylyl group, a naphthyl group, and a biphenyl group.

The halogenated hydrocarbon group is not particularly limited, and examples thereof include those in which one or more hydrogens of the hydrocarbon group are substituted with halogen{s} such as fluorine, chlorine, bromine, and iodine.

The alkoxy group is not particularly limited, and examples thereof include an alkoxy group having 1 to 6 carbon atoms. From the viewpoint of reactivity with the metal oxide, the alkoxy group has preferably 4 or less carbon atoms, more preferably 2 or less carbon atoms, still more preferably 1 carbon atom.

The halogen is not particularly limited, and examples thereof include fluorine, chlorine, bromine, and iodine, and chlorine is preferable from the viewpoint of reactivity with the metal oxide.

At least one of $R^1$, $R^2$, and $R^3$ is a hydrocarbon group having 3 or more carbon atoms or a halogenated hydrocarbon group having 3 or more carbon atoms, and from the viewpoint of catalytic activity and selectively obtaining an epoxide, the number of carbon atoms is preferably 6 or more, more preferably 8 or more, and is preferably 22 or less, more preferably 18 or less, still more preferably 12 or less.

Examples of the silylating agent include $(CH_3O)_3SiC_3H_7$, $(CH_3O)_3SiC_4H_9$, $(CH_3O)_3SiC_5H_{11}$, $(CH_3O)_3SiC_6H_{13}$, $(CH_3O)_3SiC_7H_{15}$, $(CH_3O)_3SiC_8H_{17}$, $(CH_3O)_3SiC_9H_{19}$, $(CH_3O)_3SiC_{10}H_{21}$, $(CH_3O)_3SiC_{11}H_{23}$, $(CH_3O)_3SiC_{12}H_{25}$, $(CH_3O)_3SiC_{13}H_{27}$, $(CH_3O)_3SiC_{14}H_{29}$, $(CH_3O)_3SiC_{15}H_{31}$, $(CH_3O)_3SiC_{16}H_{33}$, $(CH_3O)_3SiC_{17}H_{35}$, $(CH_3O)_3SiC_{18}H_{37}$, $(CH_3O)_3Si(CH_2)_6CH=CH_2$, and $(CH_3O)_3SiCH_2CH_2(CF_2)_7CF_3$.

The silylation treatment is not particularly limited and known methods can be adopted. For example, a method of reacting a metal oxide supporting a transition metal with the silylating agent in a solvent can be mentioned. The solvent is not particularly limited, and examples thereof include a non-polar organic solvent, preferably at least one non-polar organic solvent selected from hexane, ether, benzene, and toluene.

The blending amount of the silylating agent is preferably 0.05 parts by mass or more, more preferably 0.2 parts by mass or more, still more preferably 0.4 parts by mass or more, even still more preferably 0.6 parts by mass or more, and is preferably 40 parts by mass or less, more preferably 30 parts by mass or less, still more preferably 20 parts by mass or less, even still more preferably 10 parts by mass or less, furthermore preferably 8 parts by mass or less, with respect to 100 parts by mass of the metal oxide supporting the transition metal, from the viewpoint of reactivity with the metal oxide supporting the transition metal.

The reaction temperature is not particularly limited, but is preferably 70° C. or higher, more preferably 80° C. or higher, still more preferably 90° C. or higher, and is preferably 120° C. or lower, more preferably 110° C. or lower, from the viewpoint of reactivity.

The reaction time is not particularly limited, but is preferably 0.5 hours or more, more preferably 1 hour or more, still more preferably 1.5 hours or more, even still more preferably 2 hours or more, and is preferably 30 hours or less, more preferably 20 hours or less, still more preferably 10 hours or less, even still more preferably 7 hours or less, from the viewpoint of reactivity.

After the reaction is completed, the produced solid oxidation catalyst is filtered, washed with water if necessary, and dried. The solid oxidation catalyst after drying may be pulverized.

The amount of the transition metal (for example, W) supported in the solid oxidation catalyst is preferably 0.5% by mass or more, more preferably 1% by mass or more, still more preferably 3% by mass or more, even still more preferably 5% by mass or more, and is preferably 50% by mass or less, more preferably 25% by mass or less, still more preferably 15% by mass or less, even still more preferably 10% by mass or less, from the viewpoint of catalytic activity and selectively obtaining epoxides.

The wetting tension of the solid oxidation catalyst is preferably 30 mN/m or more, more preferably 40 mN/m or more, still more preferably 50 mN/m or more, even still more preferably 55 mN/m or more, and is preferably 73 mN/m or less, more preferably 70 mN/m or less, still more preferably 65 mN/m or less, even still more preferably 60 mN/m or less, from the viewpoint of catalytic activity and selectively obtaining epoxides.

The catalytic specific surface area of the solid oxidation catalyst is preferably 30 m$^2$/g or more, more preferably 50 m$^2$/g or more, still more preferably 80 m$^2$/g or more, and is preferably 250 m$^2$/g or less, more preferably 190 m$^2$/g or less, still more preferably 140 m$^2$/g or less, from the viewpoint of catalytic activity and selectively obtaining epoxides.

The average pore size of the solid oxidation catalyst is preferably 2 nm or more, more preferably 3 nm or more, still more preferably 4 nm or more, and is preferably 15 nm or less, more preferably 10 nm or less, still more preferably 7 nm or less, from the viewpoint of catalytic activity and selectively obtaining epoxides.

From the viewpoint of catalytic activity, the particle size of the solid oxidation catalyst is preferably 1 μm or more, more preferably 3 μm or more, still more preferably 5 μm or more, even still more preferably 7 μm or more, and is preferably 300 μm or less, more preferably 200 μm or less, still more preferably 100 μm or less, even still more preferably 30 μm or less.

Production of Epoxyalkane

In the present invention, an epoxyalkane is produced by reacting an olefin with an oxidant in the presence of the solid oxidation catalyst.

The olefin is not particularly limited, and may be a linear, branched, monocyclic, bicyclic, or polycyclic unsaturated hydrocarbon, and may be a monoolefin, a diolefin, or a polyolefin. The olefin may have various substituents containing halogen, oxygen, sulfur, or nitrogen atoms along with hydrogen and/or carbon atoms. The double bond may be at the end of the carbon chain or inside. If there are two or more double bonds, they may be conjugated or non-conjugated. One type of olefin may be used, or two or more types of olefins may be used in combination.

The olefin is preferably a linear or branched unsaturated hydrocarbon.

The carbon number of the olefin (excluding the carbon number of the substituent) is not particularly limited, and is, for example, 2 or more and 60 or less, preferably 8 or more, more preferably 12 or more, still more preferably 14 or more, even still more preferably 16 or more, and preferably 22 or less, more preferably 20 or less, still more preferably 18 or less. The method for producing an epoxyalkane of the present invention is suitable when the carbon number of the olefin is large.

Examples of the oxidant include a peroxide, a halogen acid or a salt thereof, a perhalogen acid or a salt thereof, and ozone. One type of oxidant may be used, or a plurality of oxidants may be used in combination.

Examples of the peroxides include peracids or salts thereof, non-peracid type organic peroxides, and non-peracid type inorganic peroxides. Examples of the peracid include percarboxylic acid, persulfuric acid, percarbonic acid, perphosphoric acid, and hypoperhalic acid. Examples of the percarboxylic acid include peracetic acid, perbenzoic acid, and metachloroperbenzoic acid. Examples of the hypoperhalic acid include hypoperchloric acid, hypoperbromoic acid, and hypoperiodic acid. Examples of the non-peracid type organic peroxide include tert-butyl hydroperoxide, cumene hydroperoxide, di-tert-butyl peroxide, dimethyldioxirane, acetone peroxide, methyl ethyl ketone peroxide, and hexamethylene triperoxide diamine. Examples of the non-peracid type inorganic peroxide include hydrogen peroxide, lithium peroxide, sodium peroxide, potassium peroxide, and permanganate.

Examples of the halogen acid include chloric acid, bromic acid, and iodic acid. Examples of the perhalogen acid include perchloric acid, perbromic acid, and periodic acid.

Examples of the peracid salt, halogenic acid salt, perhalogen acid salt, and permanganic acid salt include salts of alkali metals such as lithium, sodium, and potassium, salts of alkaline earth metals such as magnesium, calcium, and barium, other metal salts, and ammonium salts.

The oxidant is preferably a peroxide, more preferably hydrogen peroxide.

When the oxidant is hydrogen peroxide, its usage (solvents such as water, ethanol, and ether and concentrations thereof) is not particularly limited, and for example, an aqueous solution having a hydrogen peroxide concentration of 3 to 90% by mass is used. From the viewpoint of reactivity, the concentration of hydrogen peroxide is preferably 10% by mass or more, more preferably 25% by mass or more, still more preferably 40% by mass or more, and is preferably 85% by mass or less, more preferably 70% by mass or less, still more preferably 65% by mass or less.

The amount of the oxidant used is not particularly limited, but from the viewpoint of reactivity, the amount of the oxidant is preferably 0.2 equivalents or more, more preferably 0.5 equivalents or more, still more preferably 0.8 equivalents or more, even still more preferably 1.0 equivalent or more, and is preferably 10 equivalents or less, more preferably 5 equivalents or less, still more preferably 3 equivalents or less, even still more preferably 1.5 equivalents or less, with respect to 1 equivalent of the olefin.

The amount of the solid oxidation catalyst used is not particularly limited, but is preferably 0.5 parts by mass or more, more preferably 1 part by mass or more, still more preferably 3 parts by mass or more, even still more preferably 5 parts by mass or more, and is preferably 30 parts by mass or less, more preferably 20 parts by mass or less, still more preferably 10 parts by mass or less, even still more preferably 7 parts by mass or less, with respect to 100 parts by mass of the olefin, from the viewpoint of catalytic activity and selectively obtaining epoxides.

The reaction can be carried out in a liquid phase in the presence or absence of a solvent. It is preferable to use a solvent that is liquid at the temperature and pressure during the reaction and is substantially inactive with respect to the raw materials and products. The reaction can also be carried out, for example, in the form of a suspended bed or a fixed bed, by a batch method, a semi-continuous method or a continuous method. The reaction is preferably carried out in an atmosphere of an inert gas such as nitrogen. The order of charging the raw materials such as olefin, solid oxidation catalyst, and oxidant (for example, hydrogen peroxide) into the reaction vessel (order of charging) is arbitrary, and these may be charged all at once. In the case of performing an epoxidation of an olefin having a low reactivity, the reaction can be progressed efficiently by adopting a method of dropping an olefin into a mixture containing a solid oxidation catalyst and an oxidant (for example, hydrogen peroxide).

The reaction temperature is usually about 0 to 120° C., but from the viewpoint of reactivity, safety, and selectively obtaining epoxides, the reaction temperature is preferably 40° C. or higher, more preferably 50° C. or higher, still more preferably 60° C. or higher, and is preferably 90° C. or lower, more preferably 85° C. or lower, still more preferably 80° C. or lower.

The reaction pressure may be a pressure sufficient to keep the reaction mixture in a liquid state but is preferably a normal pressure from the viewpoint of safety.

The reaction time varies depending on the type of the solid oxidation catalyst and the olefin used, the concentration of the oxidant (for example, hydrogen peroxide), the reaction temperature, etc., but is usually several minutes to 40 hours. From the viewpoint of reactivity and productivity, the reaction time is preferably 0.5 hours or more, more preferably 1 hour or more, still more preferably 1.5 hours or more, even still more preferably 2 hours or more, and is preferably 30 hours or less, more preferably 20 hours or less, still more preferably 10 hours or less, even still more preferably 7 hours or less.

After the reaction, the solid oxidation catalyst is separated by filtration, and then water and the solvent are removed by means such as extraction or distillation to obtain a desired epoxyalkane. The solid oxidation catalyst separated by filtration can be used repeatedly.

The present invention and preferred embodiments of the present invention are described below.

<1>
A method for producing an epoxyalkane, which method comprises reacting an olefin with an oxidant in the presence of a solid oxidation catalyst, wherein
the solid oxidation catalyst comprises a transition metal and a carrier that supports the transition metal, and
the carrier is a metal oxide having a silyl group represented by the following general formula (1):

$$R^1R^2R^3Si— \quad (1)$$

wherein $R^1$, $R^2$, and $R^3$ are each independently a single bond, a hydrocarbon group, a halogenated hydrocarbon group, an alkoxy group, or a halogen, and at least one of $R^1$, $R^2$, and $R^3$ is a hydrocarbon group having 3 or more carbon atoms or a halogenated hydrocarbon group having 3 or more carbon atoms.

<2>
The method for producing an epoxyalkane according to <1>, wherein the transition metal is supported on the carrier in the form of a simple substance, a compound, or an ion.

<3>
The method for producing an epoxyalkane according to <1> or <2>, wherein the transition metal is preferably a metal element of groups 4 to 8, more preferably a group 6 metal element, still more preferably W.

<4>
The method for producing an epoxyalkane according to <2> or <3>, wherein the transition metal compound is a tungsten compound.

<5>
The method for producing an epoxyalkane according to <4>, wherein the tungsten compound is tungstic acid or a salt thereof.

<6>
The method for producing an epoxyalkane according to any one of <1> to <5>, wherein the metal oxide is preferably an oxide containing a metal element having a period of 3 to 5 cycles in the periodic table, more preferably an oxide containing one or more metal elements selected from Mg, Al, Si, Ti, Fe, Zn, Ga, Y, Zr, and Sn, still more preferably an oxide containing Al.

<7>
The method for producing an epoxyalkane according to any one of <1> to <6>, wherein the metal oxide is a composite with phosphonic acid.

<8>
The method for producing an epoxyalkane according to any one of <1> to <7>, wherein the metal oxide preferably contains phosphoric acid, more preferably contains Al and/or phosphoric acid, and is still more preferably aluminum phosphate.

<9>
The method for producing an epoxyalkane according to <7> or <8>, wherein the phosphonic acid is preferably an organic phosphonic acid having a saturated or unsaturated hydrocarbon group having 1 or more and 18 or less carbon atoms, more preferably one or more selected from an alkylphosphonic acid having an alkyl group of 2 to 18 carbon atoms and an aryl phosphonic acid, still more preferably an alkylphosphonic acid having an alkyl group of 2 to 18 carbon atoms.

<10>
The method for producing an epoxyalkane according to any one of <7> to <9>, wherein the method for preparing the composite of the metal oxide and the phosphonic acid is a precipitation method.

<11>
The method for producing an epoxyalkane according to <10>, wherein the composite of the metal oxide and the phosphonic acid is a composite of aluminum phosphate and an organic phosphonic acid ($RPOO_2AlPO_4$).

<12>
The method for producing an epoxyalkane according to <11>, wherein an aqueous solution (S) containing a water-soluble aluminum salt, phosphoric acid, and an organic phosphonic acid is mixed with an alkali (T) in the precipitation method.

<13>
The method for producing an epoxyalkane according to <12>, wherein the molar ratio (Al/P) of Al in the water-soluble aluminum salt to P in the phosphoric acid and organic phosphonic acid is preferably 0.6 or more, more preferably 0.7 or more, still more preferably 0.8 or more, even still more preferably 0.9 or more, and is preferably 10 or less, more preferably 5 or less, still more preferably 2 or less, even still more preferably less than 1.

<14>
The method for producing an epoxyalkane according to <12> or <13>, wherein the molar ratio of the organic phosphonic acid to the phosphoric acid (organic phosphonic acid/phosphoric acid) is preferably 0.05 or more, more preferably 0.1 or more, still more preferably 0.2 or more, even still more preferably 0.3 or more, and is preferably 5 or less, more preferably 3 or less, still more preferably 1 or less, even still more preferably 0.5 or less.

<15>
The method for producing an epoxyalkane according to any one of <12> to <14>, wherein the alkali (T) is ammonia.

<16>
The method for producing an epoxyalkane according to any one of <12> to <15>, wherein the method of mixing the aqueous solution (S) and the alkali (T) is a method of dropping the alkali (T) into the aqueous solution (S).

<17>
The method for producing an epoxyalkane according to <16>, wherein the dropping time is preferably 0.5 hours or more, more preferably 1 hour or more, still more preferably 2 hours or more, even still more preferably 3 hours or more, and is preferably 15 hours or less, more preferably 10 hours or less, still more preferably 5 hours or less.

<18>
The method for producing an epoxyalkane according to <16> or <17>, wherein the reaction temperature is preferably 20° C. or higher, more preferably 25° C. or higher, and is preferably 80° C. or lower, more preferably 60° C. or lower, still more preferably 40° C. or lower.

<19>
The method for producing an epoxyalkane according to any one of <12> to <18>, wherein the pH when mixing the aqueous solution (S) and the alkali (T) is preferably 4.0 or more, more preferably 4.5 or more, still more preferably 5.0 or more, and is preferably 10.0 or less, more preferably 8.0 or less, still more preferably 6.0 or less.

<20>
The method for producing an epoxyalkane according to any one of <12> to <19>, wherein the precipitate obtained by mixing the aqueous solution (S) and the alkali (T) is aged in the reaction solution.

<21>
The method for producing an epoxyalkane according to <20>, wherein the aging time is preferably 0.5 hours or more, more preferably 1 hour or more, and is preferably 10 hours or less, more preferably 5 hours or less, still more preferably 3 hours or less.

<22>
The method for producing an epoxyalkane according to <20> to <21>, wherein the precipitate is calcined.
<23>
The method for producing an epoxyalkane according to <22>, wherein the calcination temperature is preferably 250° C. or higher, more preferably 300° C. or higher, still more preferably 350° C. or higher, and is preferably 500° C. or lower, more preferably 450° C. or lower, still more preferably 400° C. or lower.
<24>
The method for producing an epoxyalkane according to <22> or <23>, wherein the calcination time is preferably 1 hour or more, more preferably 2 hours or more, still more preferably 3 hours or more, and is preferably 10 hours or less, more preferably 7 hours or less, still more preferably 5 hours or less.
<25>
The method for producing an epoxyalkane according to any one of <22> to <24>, wherein the calcination is carried out in the presence of air or oxygen.
<26>
The method for producing an epoxyalkane according to any one of <1> to <25>, wherein the carrier is in the form of a powder, and an average particle size of the powder is preferably 1 μm or more, more preferably 3 μm or more, still more preferably 5 μm or more, even still more preferably 7 μm or more, and is preferably 300 μm or less, more preferably 200 μm or less, still more preferably 100 μm or less, even still more preferably 30 μm or less.
<27>
The method for producing an epoxyalkane according to any one of <1> to <25>, wherein the carrier is in the form of granules, and an average particle size of granules is preferably 0.2 mm or more, more preferably 0.4 mm or more, still more preferably 0.6 mm or more, and is preferably 2.0 mm or less, more preferably 1.3 mm or less, still more preferably 0.8 mm or less.
<28>
The method for producing an epoxyalkane according to any one of <1> to <25>, wherein the carrier is in the form of a noodle, and a diameter of the noodle is preferably 1.0 mm or more, more preferably 1.2 mm or more, still more preferably 1.4 mm or more, and is preferably 2.5 mm or less, more preferably 2.0 mm or less, still more preferably 1.5 mm or less.
<29>
The method for producing an epoxyalkane according to any one of <1> to <25> and <28>, wherein the carrier is in the form of a noodle, and a length of the noodle is preferably 2 mm or more, more preferably 3 mm or more, and is preferably 8 mm or less, more preferably 6 mm or less, still more preferably 4 mm or less.
<30>
The method for producing an epoxyalkane according to any one of <1> to <25>, wherein the carrier is in the form of a pellet, and a length of the pellet is preferably 1.5 mm or more, more preferably 2.0 mm or more, still more preferably 2.5 mm or more, and is preferably 5.0 mm or less, more preferably 4.0 mm or less, still more preferably 3.0 mm or less.
<31>
The method for producing an epoxyalkane according to any one of <1> to <30>, wherein the specific surface area of the carrier is preferably 30 m$^2$/g or more, more preferably 50 m$^2$/g or more, still more preferably 80 m$^2$/g or more, and is preferably 250 m$^2$/g or less, more preferably 190 m$^2$/g or less, still more preferably 140 m$^2$/g or less.
<32>
The method for producing an epoxyalkane according to any one of <1> to <31>, wherein the average pore diameter of the carrier is preferably 2 nm or more, more preferably 3 nm or more, still more preferably 4 nm or more, and is preferably 15 nm or less, more preferably 10 nm or less, still more preferably 7 nm or less.
<33>
The method for producing an epoxyalkane according to any one of <1> to <32>, wherein the solid oxidation catalyst is prepared by supporting the transition metal on the metal oxide and then silylating the metal oxide with a silylating agent.
<34>
The method for producing an epoxyalkane according to <33>, wherein the transition metal is supported on the metal oxide by an impregnation method.
<35>
The method for producing an epoxyalkane according to <33> or <34>, wherein a transition metal-supported metal oxide in which the transition metal is supported on the metal oxide is calcined.
<36>
The method for producing an epoxyalkane according to <35>, wherein the calcination temperature is preferably 150° C. or higher, more preferably 200° C. or higher, still more preferably 300° C. or higher, and is preferably 500° C. or lower, more preferably 450° C. or lower, still more preferably 400° C. or lower.
<37>
The method for producing an epoxyalkane according to <35> or <36>, wherein the calcination time is preferably 1 hour or more, more preferably 2 hours or more, still more preferably 3 hours or more, and is preferably 10 hours or less, more preferably 7 hours or less, still more preferably 5 hours or less.
<38>
The method for producing an epoxyalkane according to any one of <35> to <37>, wherein the calcination is carried out in the presence of air or oxygen.
<39>
The method for producing an epoxyalkane according to any one of <33> to <38>, wherein the silylating agent is a silylating agent represented by the following general formula (2):

$$R^1R^2R^3SiX \quad (2)$$

wherein $R^1$, $R^2$, and $R^3$ are each independently a hydrocarbon group, a halogenated hydrocarbon group, an alkoxy group, or a halogen; at least one of $R^1$, $R^2$, and $R^3$ is a hydrocarbon group having 3 or more carbon atoms or a halogenated hydrocarbon group having 3 or more carbon atoms; and X is an alkoxy group or a halogen.
<40>
The method for producing an epoxyalkane according to any one of <1> to <39>, wherein the hydrocarbon group is a saturated or unsaturated aliphatic hydrocarbon group, a saturated or unsaturated alicyclic hydrocarbon group or an aromatic hydrocarbon group.
<41>
The method for producing an epoxyalkane according to <40>, wherein the number of carbon atoms of the aliphatic hydrocarbon group or the alicyclic hydrocarbon group is preferably 3 or more, more preferably 6 or more, still more preferably 8 or more, and is preferably 22 or less, more preferably 18 or less, still more preferably 12 or less.

<42>

The method for producing an epoxyalkane according to <40> or <41>, wherein the aromatic hydrocarbon group is a phenyl group, a benzyl group, a tolyl group, a xylyl group, a naphthyl group or a biphenyl group.

<43>

The method for producing an epoxyalkane according to any one of <1> to <42>, wherein the halogenated hydrocarbon group is one in which one or more hydrogens of the hydrocarbon group are substituted with fluorine, chlorine, bromine or iodine.

<44>

The method for producing an epoxyalkane according to any one of <1> to <43>, wherein the alkoxy group is an alkoxy group having 1 to 6 carbon atoms.

<45>

The method for producing an epoxyalkane according to any one of <1> to <44>, wherein the alkoxy group has preferably 4 or less carbon atoms, more preferably 2 or less carbon atoms, still more preferably 1 carbon atom.

<46>

The method for producing an epoxyalkane according to any one of <1> to <45>, wherein the halogen is fluorine, chlorine, bromine or iodine, and is preferably chlorine.

<47>

The method for producing an epoxyalkane according to any one of <1> to <46>, wherein at least one of $R^1$, $R^2$, and $R^3$ is a hydrocarbon group having 3 or more carbon atoms or a halogenated hydrocarbon group having 3 or more carbon atoms, and the number of carbon atoms is preferably 6 or more, more preferably 8 or more, and is preferably 22 or less, more preferably 18 or less, still more preferably 12 or less.

<48>

The method for producing an epoxyalkane according to any one of <33> to <47>, wherein a silylation is carried out by a method of reacting the metal oxide supporting the transition metal with the silylating agent in a solvent.

<49>

The method for producing an epoxyalkane according to <48>, wherein the solvent is at least one non-polar organic solvent selected from hexane, ether, benzene, and toluene.

<50>

The method for producing an epoxyalkane according to <48> or <49>, wherein the blending amount of the silylating agent is preferably 0.05 parts by mass or more, more preferably 0.2 parts by mass or more, still more preferably 0.4 parts by mass or more, even still more preferably 0.6 parts by mass or more, and is preferably 40 parts by mass or less, more preferably 30 parts by mass or less, still more preferably 20 parts by mass or less, even still more preferably 10 parts by mass or less, furthermore preferably 8 parts by mass or less, with respect to 100 parts by mass of the metal oxide supporting the transition metal.

<51>

The method for producing an epoxyalkane according to any one of <48> to <50>, wherein the reaction temperature is preferably 70° C. or higher, more preferably 80° C. or higher, still more preferably 90° C. or higher, and is preferably 120° C. or lower, more preferably 110° C. or lower.

<52>

The method for producing an epoxyalkane according to any one of <48> to <51>, wherein the reaction time is preferably 0.5 hours or more, more preferably 1 hour or more, still more preferably 1.5 hours or more, even still more preferably 2 hours or more, and is preferably 30 hours or less, more preferably 20 hours or less, still more preferably 10 hours or less, even still more preferably 7 hours or less.

<53>

The method for producing an epoxyalkane according to any one of <1> to <52>, wherein the amount of the transition metal supported in the solid oxidation catalyst is preferably 0.5% by mass or more, more preferably 1% by mass or more, still more preferably 3% by mass or more, even still more preferably 5% by mass or more, and is preferably 50% by mass or less, more preferably 25% by mass or less, still more preferably 15% by mass or less, even still more preferably 10% by mass or less.

<54>

The method for producing an epoxyalkane according to any one of <1> to <53>, wherein the wetting tension of the solid oxidation catalyst is preferably 30 mN/m or more, more preferably 40 mN/m or more, still more preferably 50 mN/m or more, even still more preferably 55 mN/m or more, and is preferably 73 mN/m or less, more preferably 70 mN/m or less, still more preferably 65 mN/m or less, even still more preferably 60 mN/m or less.

<55>

The method for producing an epoxyalkane according to any one of <1> to <54>, wherein the catalytic specific surface area of the solid oxidation catalyst is preferably 30 $m^2/g$ or more, more preferably 50 $m^2/g$ or more, still more preferably 80 $m^2/g$ or more, and is preferably 250 $m^2/g$ or less, more preferably 190 $m^2/g$ or less, still more preferably 140 $m^2/g$ or less.

<56>

The method for producing an epoxyalkane according to any one of <1> to <55>, wherein the average pore size of the solid oxidation catalyst is preferably 2 nm or more, more preferably 3 nm or more, still more preferably 4 nm or more, and is preferably 15 nm or less, more preferably 10 nm or less, still more preferably 7 nm or less.

<57>

The method for producing an epoxyalkane according to any one of <1> to <56>, wherein the particle size of the solid oxidation catalyst is preferably 1 µm or more, more preferably 3 µm or more, still more preferably 5 µm or more, even still more preferably 7 µm or more, and is preferably 300 µm or less, more preferably 200 µm or less, still more preferably 100 µm or less, even still more preferably 30 µm or less.

<58>

The method for producing an epoxyalkane according to any one of <1> to <57>, wherein the olefin is a linear or branched unsaturated hydrocarbon.

<59>

The method for producing an epoxyalkane according to any one of <1> to <58>, wherein the carbon number of the olefin (excluding the carbon number of the substituent) is preferably 8 or more, more preferably 12 or more, still more preferably 14 or more, even still more preferably 16 or more, and preferably 22 or less, more preferably 20 or less, still more preferably 18 or less.

<60>

The method for producing an epoxyalkane according to any one of <1> to <59>, wherein the oxidant is a peroxide.

<61>

The method for producing an epoxyalkane according to any one of <1> to <60>, wherein the oxidant is hydrogen peroxide.

<62>
The method for producing an epoxyalkane according to <61>, wherein the concentration of hydrogen peroxide in the aqueous solution is preferably 10% by mass or more, more preferably 25% by mass or more, still more preferably 40% by mass or more, and is preferably 85% by mass or less, more preferably 70% by mass or less, still more preferably 65% by mass or less.

<63>
The method for producing an epoxyalkane according to any one of <1> to <62>, wherein the amount of the oxidant used is preferably 0.2 equivalents or more, more preferably 0.5 equivalents or more, still more preferably 0.8 equivalents or more, even still more preferably 1.0 equivalent or more, and is preferably 10 equivalents or less, more preferably 5 equivalents or less, still more preferably 3 equivalents or less, even still more preferably 1.5 equivalents or less, with respect to 1 equivalent of the olefin.

<64>
The method for producing an epoxyalkane according to any one of <1> to <63>, wherein the amount of the solid oxidation catalyst used is preferably 0.5 parts by mass or more, more preferably 1 part by mass or more, still more preferably 3 parts by mass or more, even still more preferably 5 parts by mass or more, and is preferably 30 parts by mass or less, more preferably 20 parts by mass or less, still more preferably 10 parts by mass or less, even still more preferably 7 parts by mass or less, with respect to 100 parts by mass of the olefin.

<65>
The method for producing an epoxyalkane according to any one of <1> to <59>, wherein the carbon number of the olefin (excluding the carbon number of the substituent) is 8 or more and 22 or less, the oxidant is hydrogen peroxide, the concentration of hydrogen peroxide in the aqueous solution is 10% by mass or more and 85% by mass or less, the amount of hydrogen peroxide used is 0.2 equivalents or more and 10 equivalents or less with respect to 1 equivalent of the olefin, and the amount of the solid oxidation catalyst used is 0.5 parts by mass or more and 30 parts by mass or less with respect to 100 parts by mass of the olefin.

<66>
The method for producing an epoxyalkane according to any one of <1> to <59>, wherein the carbon number of the olefin (excluding the carbon number of the substituent) is 12 or more and 20 or less, the oxidant is hydrogen peroxide, the concentration of hydrogen peroxide in the aqueous solution is 25% by mass or more and 70% by mass or less, the amount of hydrogen peroxide used is 0.5 equivalents or more and 5 equivalents or less with respect to 1 equivalent of the olefin, and the amount of the solid oxidation catalyst used is 1 parts by mass or more and 20 parts by mass or less with respect to 100 parts by mass of the olefin.

<67>
The method for producing an epoxyalkane according to any one of <1> to <59>, wherein the carbon number of the olefin (excluding the carbon number of the substituent) is 14 or more and 18 or less, the oxidant is hydrogen peroxide, the concentration of hydrogen peroxide in the aqueous solution is 40% by mass or more and 65% by mass or less, the amount of hydrogen peroxide used is 0.8 equivalents or more and 3 equivalents or less with respect to 1 equivalent of the olefin, and the amount of the solid oxidation catalyst used is 3 parts by mass or more and 10 parts by mass or less with respect to 100 parts by mass of the olefin.

<68>
The method for producing an epoxyalkane according to any one of <1> to <59>, wherein the carbon number of the olefin (excluding the carbon number of the substituent) is 16 or more and 18 or less, the oxidant is hydrogen peroxide, the concentration of hydrogen peroxide in the aqueous solution is 40% by mass or more and 65% by mass or less, the amount of hydrogen peroxide used is 1.0 equivalents or more and 1.5 equivalents or less with respect to 1 equivalent of the olefin, and the amount of the solid oxidation catalyst used is 5 parts by mass or more and 7 parts by mass or less with respect to 100 parts by mass of the olefin.

<69>
The method for producing an epoxyalkane according to any one of <1> to <68>, wherein the reaction temperature when reacting the olefin with the oxidant is preferably 40° C. or higher, more preferably 50° C. or higher, still more preferably 60° C. or higher, and is preferably 90° C. or lower, more preferably 85° C. or lower, still more preferably 80° C. or lower.

<70>
The method for producing an epoxyalkane according to any one of <1> to <69>, wherein the reaction time when reacting the olefin with the oxidant is preferably 0.5 hours or more, more preferably 1 hour or more, still more preferably 1.5 hours or more, even still more preferably 2 hours or more, and is preferably 30 hours or less, more preferably 20 hours or less, still more preferably 10 hours or less, even still more preferably 7 hours or less.

<71>
A solid oxidation catalyst that is used in a method for producing an epoxyalkane by reacting an olefin with an oxidant, wherein
the solid oxidation catalyst comprises a transition metal and a carrier that supports the transition metal, and
the carrier is a metal oxide having a silyl group represented by the following general formula (1):

$$R^1R^2R^3Si- \quad (1)$$

wherein $R^1$, $R^2$, and $R^3$ are each independently a single bond, a hydrocarbon group, a halogenated hydrocarbon group, an alkoxy group, or a halogen, and at least one of $R^1$, $R^2$, and $R^3$ is a hydrocarbon group having 3 or more carbon atoms or a halogenated hydrocarbon group having 3 or more carbon atoms.

<72>
The solid oxidation catalyst according to <71>, wherein the hydrocarbon group is a saturated or unsaturated aliphatic hydrocarbon group, a saturated or unsaturated alicyclic hydrocarbon group or an aromatic hydrocarbon group.

<73>
The solid oxidation catalyst according to <72>, wherein the number of carbon atoms of the aliphatic hydrocarbon group or the alicyclic hydrocarbon group is preferably 3 or more, more preferably 6 or more, still more preferably 8 or more, and is preferably 22 or less, more preferably 18 or less, still more preferably 12 or less.

<74>
The solid oxidation catalyst according to <72> or <73>, wherein the aromatic hydrocarbon group is a phenyl group, a benzyl group, a tolyl group, a xylyl group, a naphthyl group or a biphenyl group.

<75>
The solid oxidation catalyst according to any one of <71> to <74>, wherein the halogenated hydrocarbon group is one in which one or more hydrogens of the hydrocarbon group are substituted with fluorine, chlorine, bromine or iodine.

<76>
The solid oxidation catalyst according to any one of <71> to <75>, wherein the alkoxy group is an alkoxy group having 1 to 6 carbon atoms.
<77>
The solid oxidation catalyst according to any one of <71> to <76>, wherein the alkoxy group has preferably 4 or less carbon atoms, more preferably 2 or less carbon atoms, still more preferably 1 carbon atom.
<78>
The solid oxidation catalyst according to any one of <71> to <77>, wherein the halogen is fluorine, chlorine, bromine or iodine, and is preferably chlorine.
<79>
The solid oxidation catalyst according to any one of <71> to <78>, wherein at least one of $R^1$, $R^2$, and $R^3$ is a hydrocarbon group having 3 or more carbon atoms or a halogenated hydrocarbon group having 3 or more carbon atoms, and the number of carbon atoms is preferably 6 or more, more preferably 8 or more, and is preferably 22 or less, more preferably 18 or less, still more preferably 12 or less.
<80>
The solid oxidation catalyst according to any one of <71> to <79>, wherein the transition metal is supported on the carrier in the form of a simple substance, a compound, or an ion.
<81>
The solid oxidation catalyst according to any one of <71> to <80>, wherein the transition metal is preferably a metal element of groups 4 to 8, more preferably a group 6 metal element, still more preferably W.
<82>
The solid oxidation catalyst according to <80> or <81>, wherein the transition metal compound is a tungsten compound.
<83>
The solid oxidation catalyst according to <82>, wherein the tungsten compound is tungstic acid or a salt thereof.
<84>
The solid oxidation catalyst according to any one of <71> to <83>, wherein the metal oxide is preferably an oxide containing a metal element having a period of 3 to 5 cycles in the periodic table, more preferably an oxide containing one or more metal elements selected from Mg, Al, Si, Ti, Fe, Zn, Ga, Y, Zr, and Sn, still more preferably an oxide containing Al.
<85>
The solid oxidation catalyst according to any one of <71> to <84>, wherein the metal oxide is a composite with phosphoric acid.
<86>
The solid oxidation catalyst according to any one of <71> to <85>, wherein the metal oxide preferably contains phosphoric acid, more preferably contains Al and/or phosphoric acid, and is still more preferably aluminum phosphate.
<87>
The solid oxidation catalyst according to <85> or <86>, wherein the phosphonic acid is preferably an organic phosphonic acid having a saturated or unsaturated hydrocarbon group having 1 or more and 18 or less carbon atoms, more preferably one or more selected from an alkylphosphonic acid having an alkyl group of 2 to 18 carbon atoms and an aryl phosphonic acid, still more preferably an alkylphosphonic acid having an alkyl group of 2 to 18 carbon atoms.

<88>
The solid oxidation catalyst according to any one of <71> to <87>, wherein the oxidant is a peroxide.
<89>
The solid oxidation catalyst according to any one of <71> to <88>, wherein the oxidant is hydrogen peroxide.

EXAMPLES

Hereinafter, the present invention will be specifically described based on Examples. Unless otherwise specified in the table, the content "%" of each component indicates % by mass. In addition, various measurement methods are as follows.

Calculation of Supported Amount of Tungsten

The supported amount (% by mass) of tungsten in the solid oxidation catalyst was calculated from the charged amount of the raw materials.

Measurement of Olefin Conversion Rate

After converting the reaction solution to TMS using a TMSI-H (GL Sciences Inc.), a column "Ultra ALLOY-1HT" (manufactured by Frontier Laboratories Ltd.: Capillary column 30.0 m×250 μm×0.15 mm) was attached to a gas chromatograph analyzer "GC6850" (manufactured by Agilent). Analysis was performed using a hydrogen flame ion detector (FID) under the conditions of an injection temperature of 300° C., a detector temperature of 350° C., and a He flow rate of 4.6 mL/min, and then the product was quantified. The olefin conversion rate was calculated by the following formula.

Olefin conversion rate (%)=[100−(Amount of olefin)]/[(Amount of olefin)+(Amount of epoxide)+(Total amount of by-products)]×100

Measurement of Selectivity for Epoxides

The selectivity for epoxides was calculated by the following formula. For each amount in the formula, the value obtained from the gas chromatograph analysis of the olefin conversion rate measurement was used.

Selectivity for epoxides (%)=(Amount of epoxide)/ [(Amount of olefin)+(Amount of epoxide)+(Total amount of by-products)]×100

Example 1

Preparation of Composite of Ethylphosphonic Acid with Aluminum Phosphate

In a 2 L separable flask, 600 g of ion-exchange water, 7.4 g (0.07 mol) of ethylphosphonic acid, 20.7 g (0.18 mol) of 85% aqueous phosphoric acid solution, and a solution prepared by dissolving 84 g (0.2 mol) of $Al(NO_3)_3 \cdot 9H_2O$ in 150 g of ion-exchange water were charged, and then a stirrer, a pH electrode, a thermometer, and a dropping tube holder were attached to the flask. After stirring the mixture at 25° C. and 400 rpm for 10 minutes, a 10% aqueous $NH_3$ solution was added dropwise at 25° C. using a dropping tube pump at a rate of 0.6 mL/min over the period of 3 hours until the pH reached 5. After completion of the dropping, the mixture was aged for 1 hour with stirring. Thereafter, a white cake collected by filtration under reduced pressure was washed five times with 1.5 L of ion-exchange water until the electric conductivity reached 40 mS/m (each stirring was performed at 700 rpm for 1 hour). Then, the obtained cake was dried at 120° C. overnight (about 15 hours), pulverized in a coffee mill, and further calcined at 350° C. for 3 hours to obtain a composite ($EtPOO_2Al\,PO_4$) of ethylphosphonic acid with aluminum phosphate.

Preparation of W-Supported Composite

In a 300 mL four-necked flask, 200 g of ion-exchange water and 1.0 g of tungstic acid ($H_2WO_4$) were charged, and a 28% aqueous $NH_3$ solution was added little by little until the pH reached 7 while stirring, thereby to obtain an aqueous ammonium tungstate solution. The prepared aqueous ammonium tungstate solution (200 g) was added to a 1 L round-bottom flask charged with 20 g of the composite, and the flask was immersed in an oil bath set at 63° C. and stirred for 0.5 hours. Next, water was removed from the flask by an evaporator to collect a solid. The obtained solid was dried at 120° C. overnight (about 15 hours), pulverized by a coffee mill, and calcined at 350° C. for 3 hours to obtain a W-supported composite ($W/EtPOO_2AlPO_4$) having tungsten supported on a composite.

Preparation of Solid Oxidation Catalyst

A 300 mL round-bottom flask was charged with 10 g of a W-supported composite ($W/EtPOO_2AlPO_4$), 157 g of toluene, and 1.0 g of trimethoxyoctenylsilane (($CH_3O)_3Si(CH_2)_6CH=CH_2$) as a silylating agent and was equipped with a stirrer and a thermometer. Then, the mixture was refluxed and stirred at 300 rpm for 7 hours. After allowing to stand for cooling, the mixture was filtered under reduced pressure to collect a solid, which was washed with 150 ml of ion-exchange water three times. After that, the solid was dried at 120° C. overnight (about 15 hours) to obtain a solid oxidation catalyst ($W/EtPOO_2AlPO_4Si(CH_2)_6CH=CH_2$).

Synthesis of Epoxyalkane

In a 100 mL four-neck flask, 2 g of the prepared solid oxidation catalyst ($W/EtPOO_2AlPO_4Si(CH_2)_6CH=CH_2$) and 40 g (0.18 mol) of 1-hexadecene were charged. The flask was equipped with a stirrer, a thermometer, and an $N_2$ flow, and 12 g (0.21 mol, 1.2 equivalents/1 equivalent of olefin) of 60% aqueous hydrogen peroxide was added in the flask. Thereafter, the flask was immersed in an oil bath set at 80° C. and the reaction was performed for 8 hours to synthesize epoxyhexadecane. The stirring was stopped on the way and sampling was performed every 0.5 to 2 hours to determine the olefin conversion rate and the selectivity for epoxides by the method described above. Table 1 shows the olefin conversion rate and the selectivity for epoxides at the reaction times shown in Table 1.

Example 2

A solid oxidation catalyst ($W/EtPOO_2AlPO_4SiC_8H_{17}$) was obtained in the same manner as in Example 1 except that 0.2 g of trimethoxyoctylsilane was used as the silylating agent in the preparation of the solid oxidation catalyst.
Then, using the solid oxidation catalyst ($W/EtPOO_2AlPO_4SiC_8H_{17}$), epoxyhexadecane was synthesized by the same method as in Example 1 except that the reaction time was changed to that shown in Table 1. Then, an olefin conversion rate and a selectivity for epoxides were determined and the results were described in Table 1.

Example 3

A solid oxidation catalyst ($W/EtPOO_2AlPO_4SiC_8H_{17}$) was obtained in the same manner as in Example 1 except that 1.0 g of trimethoxyoctylsilane was used as the silylating agent in the preparation of the solid oxidation catalyst.
Then, using the solid oxidation catalyst ($W/EtPOO_2AlPO_4SiC_8H_{17}$), epoxyhexadecane was synthesized by the same method as in Example 1 except that the reaction time was changed to that shown in Table 1. Then, an olefin conversion rate and a selectivity for epoxides were determined and the results were described in Table 1.

Examples 4 to 11 and Comparative Example 2

Preparation of Aluminum Phosphate

In a 2 L separable flask, 600 g of ion-exchange water, 25.8 g (0.22 mol) of an 85% aqueous phosphoric acid solution, and a solution in which 84 g (0.2 mol) of $Al(NO_3)_3 \cdot 9H_2O$ was dissolved in 150 g of ion-exchange water were charged, and a stirrer, a pH electrode, a thermometer, and a dropping tube holder were attached to the flask. After stirring the mixture at 25° C. and 400 rpm for 10 minutes, a 10% aqueous $NH_3$ solution was added dropwise at 25° C. using a dropping tube pump at a rate of 0.6 mL/min over 3 hours until the pH reached 5. After completion of the dropwise addition, the mixture was aged for 1 hour with stirring. Thereafter, a white cake collected by filtration under reduced pressure was washed five times with 1.5 L of ion-exchange water until the electric conductivity reached 40 mS/m (each stirring was performed at 700 rpm for 1 hour). Then, the obtained cake was dried at 120° C. overnight (about 15 hours), pulverized by a coffee mill, and further calcined at 350° C. for 3 hours to obtain aluminum phosphate ($AlPO_4$).

Preparation of W-Supported Aluminum Phosphate

In a 300 mL four-necked flask, 200 g of ion-exchange water and 1.0 g of tungstic acid ($H_2WO_4$) were charged, and a 28% aqueous $NH_3$ solution was added little by little until the pH reached 7 while stirring, thereby to obtain an aqueous ammonium tungstate solution. The prepared aqueous ammonium tungstate solution (200 g) was added to a 1 L round-bottom flask charged with 20 g of the prepared aluminum phosphate, and the flask was immersed in an oil bath set at 63° C. and stirred for 0.5 hours. Next, water was removed from the flask by an evaporator to collect a solid. The obtained solid was dried at 120° C. overnight (about 15 hours), pulverized by a coffee mill, and calcined at 350° C. for 3 hours to obtain a W-supported aluminum phosphate ($W/AlPO_4$) having tungsten supported on aluminum phosphate.

Preparation of Solid Oxidation Catalyst

Each solid oxidation catalyst ($W/AlPO_4SiR$) shown in Table 1 was obtained in the same manner as in Example 1 except that the silylating agent and the blending amount shown in Table 1 were used.

Synthesis of Epoxyalkane

Epoxyhexadecane was synthesized in the same manner as in Example 1 except that each solid oxidation catalyst (W/AlPO$_4$SiR) shown in Table 1 was used and the reaction time was changed to that shown in Table 1. Then, an olefin conversion rate and a selectivity for epoxides were determined and the results were shown in Table 1. It should be noted that in Example 9, 200 parts by mass of t-butyl alcohol was used with respect to 100 parts by mass of 1-hexadecene.

Comparative Example 1

Synthesis of Epoxyalkane

Epoxyhexadecane was synthesized in the same manner as in Example 1 except that the prepared W-supported aluminum phosphate (W/AlPO$_4$) was used and the reaction time was changed to that shown in Table 1. Then, an olefin conversion rate and a selectivity for epoxides were determined and the results were shown in Table 1.

Comparative Example 3

Preparation of Catalyst

A round bottom flask having a capacity of 30 cm$^3$ was charged with 0.387 g (3 mmol) of quinoline, 0.596 g (3 mmol) of chloropropyltrimethoxysilane and 5 cm$^3$ of petroleum ether, and the mixture was vigorously stirred in a hot water bath at 70° C. under a nitrogen atmosphere for 5 hours. After completion of the stirring, 5 cm$^3$ of dry ethanol and 3 g of silica gel were added thereto, and the mixture was vigorously stirred at the same temperature for another 1 hour. After completion of the stirring, the reaction solution was cooled to room temperature. Then, 2.88 g (1 mmol) of 12-tungstophosphoric acid dissolved in 5 cm$^3$ of dry ethanol was added, and the mixture was vigorously stirred at room temperature for 5 hours under a nitrogen atmosphere. After the stirring was completed, the solvent was distilled off at 50° C. under reduced pressure (133 Pa). Then, the residue was dried for 5 hours under reduced pressure (133 Pa) under a nitrogen atmosphere to prepare a catalyst.

Synthesis of Epoxyalkane

Epoxyhexadecane was synthesized in the same manner as in Example 1 except that the prepared catalyst was used and the reaction time was changed to that shown in Table 1. Then, an olefin conversion rate and a selectivity for epoxides were determined and the results were shown in Table 1.

TABLE 1

| | | UNIT | EXAMPLE 1 | EXAMPLE 2 | EXAMPLE 3 | EXAMPLE 4 |
|---|---|---|---|---|---|---|
| CARRIER | | — | — | EtPOO$_2$AlPO$_4$ | | AlPO$_4$ |
| SOLID OXIDATION CATALYST | | — | — | W/EtPOO$_2$AlPO$_4$SiR | | W/AlPO$_4$SiR |
| R GROUP OF SILYLATING AGENT (MeO)$_3$SiR | | — | Octeny | Octyl | Octyl | Propyl |
| CARBON NUMBER OF R IN SILYLATING AGENT (MeO)$_3$SiR | | — | C8 | C8 | C8 | C3 |
| NON-IONIC/IONIC | | — | NON-IONIC | NON-IONIC | NON-IONIC | NON-IONIC |
| AMOUNT OF SILYLATING AGENT (VS W-SUPPORTED CATALYST AMOUNT) | | % BY MASS | 10 | 2 | 10 | 10 |
| W-SUPPORTED AMOUNT | | % BY MASS | 3.5 | 3.5 | 3.5 | 3.5 |
| REACTION TEMPERATURE | | ° C. | 80 | 80 | 80 | 80 |
| REACTION TIME | | hr | 4 | 6.25 | 2 | 2 |
| OLEFIN CONVERSION RATE | | % | 18 | 15 | 18 | 17 |
| SELECTIVITY FOR EPDXIDES | | % | 60 | 65 | 59 | 55 |
| PREPATION OF CARRIER | AMOUNT OF ETHYLPHOSPHONIC ACID | g | 7.4 | 7.4 | 7.4 | — |
| | MOLE OF ETHYLPHOSPHONIC ACID | mol | 0.07 | 0.07 | 0.07 | — |
| | AMOUNT OF 85% PHOSPHORIC ACID | g | 20.7 | 20.7 | 20.7 | 25.8 |
| | MOLE OF PHOSPHORIC ACID | mol | 0.18 | 0.18 | 0.18 | 0.22 |
| | AMOUNT OF ION-EXCHANGE WATER | g | 600 | 600 | 600 | 600 |
| | AMOUNT OF ALUMINUM NITRATE | g | 84 | 84 | 84 | 84 |
| | MOLE OF ALUMINUM NITRATE | mol | 0.2 | 0.2 | 0.2 | 0.2 |

TABLE 1-continued

| | | | | | | | |
|---|---|---|---|---|---|---|---|
| PREPARATION OF W-SUPPORTED CATALYST | PREPARATION OF IMPREGNATION SOLUTION | AMOUNT OF ION-EXCHANGE WATER (FOR DISSOLVING ALUMINUM NITRATE) | g | 150 | 150 | 150 | 150 |
| | | AMOUNT OF $H_2WO_4$ | g | 1.0 | 1.0 | 1.0 | 1.0 |
| | | AMOUNT OF ION-EXCHANGE WATER | g | 200 | 200 | 200 | 200 |
| | IMPREGNATION OF W | AMOUNT OF CARRIER | g | 20 | 20 | 20 | 20 |
| | | $H_2WO_4 + NH_3$ AQ. SOLUTION | g | 200 | 200 | 200 | 200 |
| SILYLATION TREATMENT | | AMOUNT OF W-SUPPORTED CATALYST | g | 10 | 10 | 10 | 10 |
| | | AMOUNT OF SILYLATING AGENT (VS AMOUNT OF SUPPORTED CATALYST) | g | 1.0 | 0.2 | 1.0 | 1.0 |
| | | AMOUNT OF TOLUEN (15.7 TIMES THE AMOUNT OF W-SUPPORTED CATALYST) | g | 157 | 157 | 157 | 157 |

| | | EXAMPLE 5 | EXAMPLE 6 | EXAMPLE 7 | EXAMPLE 8 | EXAMPLE 9 |
|---|---|---|---|---|---|---|
| CARRIER | | | | $AlPO_4$ | | |
| SOLID OXIDATION CATALYST | | | | $W/AlPO_4SiR$ | | |
| R GROUP OF SILYLATING AGENT $(MeO)_3SiR$ | | Hexyl | Dodecyl | Dodecyl | Dodecyl | Dodecyl |
| CARBON NUMBER OF R IN SILYLATING AGENT $(MeO)_3SiR$ | | C6 | C12 | C12 | C12 | C12 |
| NON-IONIC/IONIC | | NON-IONIC | NON-IONIC | NON-IONIC | NON-IONIC | NON-IONIC |
| AMOUNT OF SILYLATING AGENT (VS W-SUPPORTED CATALYST AMOUNT) | | 10 | 2 | 5 | 10 | 10 |
| W-SUPPORTED AMOUNT | | 3.5 | 3.5 | 3.5 | 3.5 | 3.5 |
| REACTION TEMPERATURE | | 80 | 80 | 80 | 80 | 80 |
| REACTION TIME | | 2 | 2 | 4 | 2 | 2 |
| OLEFIN CONVERSION RATE | | 14 | 16 | 18 | 15 | 20 |
| SELECTIVITY FOR EPDXIDES | | 62 | 62 | 57 | 63 | 57 |
| PREPATION OF CARRIER | AMOUNT OF ETHYLPHOSPHONIC ACID | — | — | — | — | — |
| | MOLE OF ETHYLPHOSPHONIC ACID | — | — | — | — | — |
| | AMOUNT OF 85% PHOSPHORIC ACID | 25.8 | 25.8 | 25.8 | 25.8 | 25.8 |
| | MOLE OF PHOSPHORIC ACID | 0.22 | 0.22 | 0.22 | 0.22 | 0.22 |
| | AMOUNT OF ION-EXCHANGE WATER | 600 | 600 | 600 | 600 | 600 |
| | AMOUNT OF ALUMINUM NITRATE | 84 | 84 | 84 | 84 | 84 |
| | MOLE OF ALUMINUM NITRATE | 0.2 | 0.2 | 0.2 | 0.2 | 0.2 |

TABLE 1-continued

| | | | | | | | |
|---|---|---|---|---|---|---|---|
| PREPARATION OF W-SUPPORTED CATALYST | PREPARATION OF IMPREGNATION SOLUTION | AMOUNT OF ION-EXCHANGE WATER (FOR DISSOLVING ALUMINUM NITRATE) | 150 | 150 | 150 | 150 | 150 |
| | | AMOUNT OF H$_2$WO$_4$ | 1.0 | 1.0 | 1.0 | 1.0 | 1.0 |
| | | AMOUNT OF ION-EXCHANGE WATER | 200 | 200 | 200 | 200 | 200 |
| | IMPREGNATION OF W | AMOUNT OF CARRIER | 20 | 20 | 20 | 20 | 20 |
| | | H$_2$WO$_4$ + NH$_3$ AQ. SOLUTION | 200 | 200 | 200 | 200 | 200 |
| SILYLATION TREATMENT | | AMOUNT OF W-SUPPORTED CATALYST | 10 | 10 | 10 | 10 | 10 |
| | | AMOUNT OF SILYLATING AGENT (VS AMOUNT OF SUPPORTED CATALYST) | 1.0 | 0.2 | 0.5 | 1.0 | 1.0 |
| | | AMOUNT OF TOLUEN (15.7 TIMES THE AMOUNT OF W-SUPPORTED CATALYST) | 157 | 157 | 157 | 157 | 157 |

| | | EXAMPLE 10 | EXAMPLE 11 | COMPARATIVE EXAMPLE 1 | COMPARATIVE EXAMPLE 2 | COMPARATIVE EXAMPLE 3 |
|---|---|---|---|---|---|---|
| CARRIER | | AlPO$_4$ | | | AlPO$_4$ | |
| SOLID OXIDATION CATALYST | | W/AlPO$_4$SiR | | W/AlPO$_4$ | W/AlPO$_4$SiR | |
| R GROUP OF SILYLATING AGENT (MeO)$_3$SiR | | Octadcyl | CH$_2$CH$_2$(CF$_2$)$_7$CF$_3$ | — | Ethyl | Chloropropyl |
| CARBON NUMBER OF R IN SILYLATING AGENT (MeO)$_3$SiR | | C18 | C10 | — | C2 | C3 |
| NON-IONIC/IONIC | | NON-IONIC | NON-IONIC | NON-IONIC | NON-IONIC | IONIC |
| AMOUNT OF SILYLATING AGENT (VS W-SUPPORTED CATALYST AMOUNT) | | 2 | 2 | 0 | 10 | 10 |
| W-SUPPORTED AMOUNT | | 3.5 | 3.5 | 3.5 | 3.5 | 37.5 |
| REACTION TEMPERATURE | | 80 | 80 | 80 | 80 | 80 |
| REACTION TIME | | 2 | 8 | 8 | 2 | 8 |
| OLEFIN CONVERSION RATE | | 15 | 13 | 0 | 16 | 0 |
| SELECTIVITY FOR EPDXIDES | | 64 | 65 | 0 | 43 | 0 |
| PREPATION OF CARRIER | AMOUNT OF ETHYLPHOSPHONIC ACID | — | — | — | — | — |
| | MOLE OF ETHYLPHOSPHONIC ACID | — | — | — | — | — |
| | AMOUNT OF 85% PHOSPHORIC ACID | 25.8 | 25.8 | 25.8 | 25.8 | — |
| | MOLE OF PHOSPHORIC ACID | 0.22 | 0.22 | 0.22 | 0.22 | — |
| | AMOUNT OF ION-EXCHANGE WATER | 600 | 600 | 600 | 600 | — |
| | AMOUNT OF ALUMINUM NITRATE | 84 | 84 | 84 | 84 | — |

TABLE 1-continued

| | | | | | | | |
|---|---|---|---|---|---|---|---|
| PREPARATION OF W-SUPPORTED CATALYST | PREPARATION OF IMPREGNATION SOLUTION | MOLE OF ALUMINUM NITRATE | 0.2 | 0.2 | 0.2 | 0.2 | — |
| | | AMOUNT OF ION-EXCHANGE WATER (FOR DISSOLVING ALUMINUM NITRATE) | 150 | 150 | 150 | 150 | — |
| | | AMOUNT OF H$_2$WO$_4$ | 1.0 | 1.0 | 1.0 | 1.0 | — |
| | | AMOUNT OF ION-EXCHANGE WATER | 200 | 200 | 200 | 200 | — |
| | IMPREGNATION OF W | AMOUNT OF CARRIER | 20 | 20 | 20 | 20 | — |
| | | H$_2$WO$_4$ + NH$_3$ AQ. SOLUTION | 200 | 200 | 200 | 200 | — |
| SILYLATION TREATMENT | | AMOUNT OF W-SUPPORTED CATALYST | 10 | 10 | — | 10 | — |
| | | AMOUNT OF SILYLATING AGENT (VS AMOUNT OF SUPPORTED CATALYST) | 0.2 | 0.2 | — | 1.0 | — |
| | | AMOUNT OF TOLUEN (15.7 TIMES THE AMOUNT OF W-SUPPORTED CATALYST) | 157 | 157 | — | 157 | — |

INDUSTRIAL APPLICABILITY

The method for producing an epoxyalkane and the solid oxidation catalyst according to the present invention are useful for producing an epoxyalkane for a variety of uses.

The invention claimed is:

1. A method for producing an epoxyalkane, which method comprises reacting an olefin with an oxidant in the presence of a solid oxidation catalyst, wherein
the solid oxidation catalyst comprises a transition metal and a carrier that supports the transition metal, and
the carrier is a metal oxide having a silyl group represented by the following general formula (1):

$$R^1R^2R^3Si— \quad (1)$$

wherein $R^1$, $R^2$, and $R^3$ are each independently a single bond, a hydrocarbon group, a halogenated hydrocarbon group, an alkoxy group, or a halogen, and at least one of $R^1$, $R^2$, and $R^3$ is a hydrocarbon group having 3 or more carbon atoms or a halogenated hydrocarbon group having 6 or more carbon atoms.

2. The method for producing an epoxyalkane according to claim 1, wherein at least one of $R^1$, $R^2$, and $R^3$ in the general formula (1) is a hydrocarbon group having 6 or more carbon atoms or a halogenated hydrocarbon group having 6 or more carbon atoms.

3. The method for producing an epoxyalkane according to claim 1, wherein the transition metal is W.

4. The method for producing an epoxyalkane according to claim 1, wherein the metal oxide contains Al and/or phosphoric acid.

5. The method for producing an epoxyalkane according to claim 1, wherein the metal oxide is AlPO$_4$.

6. The method for producing an epoxyalkane according to claim 1, wherein the olefin has 8 or more carbon atoms.

7. The method for producing an epoxyalkane according to claim 1, wherein the temperature at the time of the reaction is 40° C. or higher and 90° C. or lower.

8. The method for producing an epoxyalkane according to claim 1, wherein the oxidant is a peroxide.

9. The method for producing an epoxyalkane according to claim 1, wherein the oxidant is hydrogen peroxide.

10. A solid oxidation catalyst that is used in a method for producing an epoxyalkane by reacting an olefin with an oxidant, wherein
the solid oxidation catalyst comprises a transition metal and a carrier that supports the transition metal, and
the carrier is a metal oxide having a silyl group represented by the following general formula (1):

$$R^1R^2R^3Si— \quad (1)$$

wherein $R^1$, $R^2$, and $R^3$ are each independently a single bond, a hydrocarbon group, a halogenated hydrocarbon group, an alkoxy group, or a halogen, and at least one of $R^1$, $R^2$, and $R^3$ is a hydrocarbon group having 3 or more carbon atoms or a halogenated hydrocarbon group having 6 or more carbon atoms.

11. The solid oxidation catalyst according to claim 10, wherein at least one of $R^1$, $R^2$, and $R^3$ in the general formula (1) is a hydrocarbon group having 6 or more carbon atoms or a halogenated hydrocarbon group having 6 or more carbon atoms.

12. The solid oxidation catalyst according to claim 10, wherein the transition metal is W.

13. The solid oxidation catalyst according to claim 10, wherein the metal oxide contains Al and/or phosphoric acid.

14. The solid oxidation catalyst according to claim 10, wherein the metal oxide is $AlPO_4$.

15. The method for producing an epoxyalkane according to claim 2, wherein the transition metal is W.

16. The method for producing an epoxyalkane according to claim 2, wherein the metal oxide contains Al and/or phosphoric acid.

17. The method for producing an epoxyalkane according to claim 2, wherein the metal oxide is $AlPO_4$.

18. The method for producing an epoxyalkane according to claim 2, wherein the olefin has 8 or more carbon atoms.

19. The method for producing an epoxyalkane according to claim 2, wherein the temperature at the time of the reaction is 40° C. or higher and 90° C. or lower.

20. The method for producing an epoxyalkane according to claim 2, wherein the oxidant is a peroxide.

* * * * *